United States Patent [19]

Ochsner

[11] Patent Number: 4,668,433
[45] Date of Patent: May 26, 1987

[54] NOVEL DERIVATIVES OF 6-HYDROXYHEXANOATES AS FRAGRANCE INGREDIENTS

[75] Inventor: Paul A. Ochsner, Geneva, Switzerland

[73] Assignee: Givaudan Corporation, Clifton, N.J.

[21] Appl. No.: 783,595

[22] Filed: Oct. 3, 1985

[30] Foreign Application Priority Data

Aug. 6, 1984 [CH] Switzerland ................. 3370/85
Oct. 10, 1984 [CH] Switzerland ................. 4856/84

[51] Int. Cl.[4] .................... A61K 7/46; C11B 9/00
[52] U.S. Cl. .................... 252/522 R; 560/185; 560/187
[58] Field of Search .......... 252/522 R; 560/185, 560/187

[56] References Cited

U.S. PATENT DOCUMENTS 3,809,712  5/1974  Yetter ..................... 560/185
3,929,847 12/1975  Snapp et al. .............. 560/185
4,110,626  8/1978  Katoda et al. ............. 252/522 R

FOREIGN PATENT DOCUMENTS 517212  10/1955  Canada ........................ 560/185
1960716  7/1971  Fed. Rep. of Germany ......... 560/185
1198414  7/1970  United Kingdom ............... 560/185
1242980  8/1971  United Kingdom ............... 560/185

OTHER PUBLICATIONS

S. Arctander, "Perfume and Flavor Chemicals", Montclair, NJ, (1969), No. 1143.
J. Hamonet, Bull. Soc. Chim. [3], 33 (1905) 533–541.

Primary Examiner—Werren B. Lone
Attorney, Agent, or Firm—Robert F. Tavares

[57] ABSTRACT

Compounds of the formula

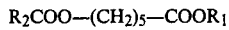

$$R_2COO-(CH_2)_5-COOR_1$$

wherein:
  $R_1$ is a one to four carbon alkyl group or a two to three carbon alkenyl group, and
  $R_2$ is hydrogen, a one to three carbon alkyl group, a two or three carbon alkenyl group, methoxy or ethoxy, and fragrance compositions containing them.

19 Claims, No Drawings

NOVEL DERIVATIVES OF 6-HYDROXYHEXANOATES AS FRAGRANCE INGREDIENTS

THE INVENTION

This invention is concerned with novel compounds of the formula

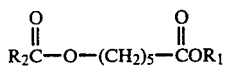     I wherein:
R$_1$ is chosen from the group consisting of alkyl radicals having one to four carbon atoms and alkenyl radicals having two to four carbon atoms, and
R$_2$ is chosen from the group consisting of hydrogen, alkyl radicals having one to three carbon atoms, alkenyl radicals having two to three carbon atoms, methoxy and ethoxy.

The invention is also concerned with fragrance compositions containing these novel compounds of formula I and a process for the manufacture of the compounds.

DESCRIPTION OF THE PREFERRED EMBODIMENTS

The alkyl and alkenyl radicals represented by R$_1$ and R$_2$ can be normal straight-chain radicals or branched radicals. Typical examples of such radicals are methyl, ethyl, propyl, isopropyl, butyl, isobutyl, vinyl, allyl, propenyl, methallyl, and the like. It should also be understood that formula I is intended to embrace all geometric isomers which are possible.

The compounds I have particularly valuable organoleptic properties and are especially useful as odorant substances. This invention is, therefore, also concerned with the use of the compounds as odorant substances.

Among the especially preferred compounds are ethyl 6-acetoxyhexanoate, ethyl 6-isobutyryloxy-hexanoate and allyl 6-propionyloxy-hexanoate. Also preferred are methyl 6-formyloxy-hexanoate, allyl 6-formyloxy-hexanoate, isobutyl 6-formyloxy-hexanoate, allyl 6-acetoxy-hexanoate, isobutyl 6-acetoxy-hexanoate and ethyl 6-ethoxycarbonyloxy-hexanoate.

The invention is also concerned with a process for the manufacture of the compounds I. Said process comprising the esterification of a compound of the formula

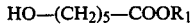     (II)

wherein R$_1$ has the above significance.

The esterification of the alcohols II is carried out by using the usual acylating agents, e.g. acyl halides or acid anhydrides. The procedure using the acid anhydrides is preferred. The procedure using the acid anhydrides is preferably carried out in the presence of phosphoric acid. The reaction using acyl halides is preferably carried out in the presence of tertiary amines such as pyridine or N,N-dimethylaniline.

The carbonate esters I (R$_2$=methoxy or ethoxy) are manufactured in a manner similar to methods known in the art by reacting the alcohols II with chloroformic acid esters in the presence of tertiary amines such as pyridine or N,N-dimethylaniline.

The esters I are conveniently purified by distillation under reduced pressure. They are colorless to slightly yellow colored liquids. They are insoluble in water, but soluble in organic solvents such as e.g. alcohols, ethers, ketones, esters, hydrocarbons and halogenated hydrocarbons.

As mentioned above, the compounds of general formula I have particularly valuable organoleptic properties and are distinquished, in particular, by a combination of fruity notes and pronounced tenacity. They also can be used to intensify woody musk notes of odorant substance compositions without, at the same time, interfering with their individual odor.

Of particular interest are the raspberry notes, which are particularly pronounced in ethyl 6-acetoxy-hexanoate and ethyl 6-isobutyryloxy-hexanoate. While a number of substances having a raspberry odor are already known, e.g. piperonylacetone or p-hydroxybenzylacetone, these are, without exception, compounds which are many times more expensive to produce based on structural considerations.

It is a surprising and unexpected finding that in the case of ethyl 6-acetoxy-hexanoate and ethyl 6-ethoxycarbonyloxy-hexanoate the woody note characteristic of conventional raspberry compositions is now intensified and a pronounced fixative effect occurs without at the same time, having a detrimental effect on the fruity notes.

The other compounds of structure I are also distinquished by fruity notes, although in certain cases flowery side-notes are also noted. Of special interest are methyl 6-propionyloxy-hexanoate (narcissus) and isobutyl 6-acetoxy-hexanoate (after nerolidol).

Based on their olfactory notes, the compounds of formula I are particularly suitable for the intensification of fruity notes and as intensifiers of musk notes. Moreover, they are suitable for modifying an extremely wide range of known compositions, e.g.

(a) flowery compositions in which e.g. the warm musk notes are to be intensified (e.g. for men's colognes),
(b) chypre compositions (extract types, compositions of the feminine direction),
(c) tobacco and woody and fougere compositions (extract types of the masculine direction), and
(d) compositions with green notes, where especially a desired intensification and rounding-off and harmonizing effect are achieved.

As odorant substances the compounds of formula I are particularly suitable, in combination with a series of natural and synthetic odorant substances, such as e.g.

Natural Products

Such as angelica root oil, galbanum oil, vetiver oil, patchouli oil, sandalwood oil, mandarin oil, muscatel sage, ylang-ylang oil, cedar oil, pine oil, lavendar oil, bergamot oil, lemon oil, orange oil, coriander oil, oak moss, castoreum, ciste labdanum, calmus oil, geranium oil, jasmine absolute, rose oil, cassis absolute, narcissus absolute, verveine absolute, grapefruit extracts, etc.

Aldehydes

Such as C$_{10}$-, C$_{11}$-, C$_{14}$-aldehyde, hydroxycitronellal, cyclamen aldehyde, benzaldehyde, p-tert.-butyl-α-methyl-hydrocinnamaldehyde, citral, citronellal, 2,6-dimethyl-5-hepten-1-al, isovaleraldehyde, trans-2-hexenal, trans-2-octenal, n-octanal, n-nonanal, trans-2-cis-6-nonadienal, 2,4-decadienal, methylnonyl-acetaldehyde, Cyclal C (1,3-dimethylcyclohex-1-ene 4(and 5)-carboxaldehyde), 3 and 4-(4-methyl-4-hydroxyamyl)-Δ3-cyclohexenecarboxaldehyde, etc.

Ketones

Such as alpha-ionone, beta-ionone, methylionone, allylionone, acetanisole, 4-(para-hydroxyphenyl)-2-butanone, camphor, menthone, carvone, pulegone, p-methylacetophenone, methyl amyl ketone, etc.

Acetals and ketals

Such as phenylacetaldehyde dimethyl acetal, phenylacetaldehyde glycerine acetal, 2-methyl-1,3-dioxolan-2-ethyl acetate, caproic aldehyde dimethyl acetal, Acetal R (mixed acetal of acetaldehyde with phenylethyl alcohol and n-propanol), etc.

Ethers

Such as eugenol methyl ether, methyl 1-methylcyclododecyl ether, anethol, estragol, rosantolene (methylethylsaligenin), etc.

Phenolic substances

Such as vanillin, eugenol, creosol, chavicol, etc.

Alcohols

Such as butanol, n-hexanol, cis-3-hexenol, trans-2-cis-6-nonadienol, cis-6-nonenol, linalool, geraniol, rhodinol, nerol, citronellol, nerolidol, farnesol, benzyl alcohol, phenylethyl alcohol, cinnamylalcohol, terpineol, Patchone (4-tert.-butylcyclohexanol), etc.

Esters

Such as ethyl formate, ethyl acetate, isoamyl acetate, t-butylcyclohexyl acetate, Myraldylacetat® (Givaudan), benzyl acetate, styrallyl acetate, ethyl α-methylphenylglycidate, maltyl isobutyrate, dimethylbenzylcarbinyl acetate and butyrate, linalyl acetate, isobutyl acetate, n-amyl butyrate, n-amyl valerate, ethyl palmitate, cinnamyl formate, terpenyl acetate, geranyl acetate, hexyl salicylate, linalyl anthranilate, amyl salicylate, methyl dihydrojasmonate, benzyl salicylate.

Lactones

Such as γ-undecalactone, γ-decalactone, γ-nonalactone, δ-decalactone, δ-octalactone, coumarin, etc.

Acids

Such as geranylic acid, citronellylic acid, cinnamic acid, phenylacetic acid, etc.

Sulphur-containing compounds

Such as p-menthane-8-thiol-3-one, dimethyl sulphide and other sulphides and disulphides, etc.

Nitrogen-containing compounds

Such as methyl anthranilate, indole, isobutylquinoline, various pyrazines, 5-methyl-heptan-3-one oxime, nitromusk, etc.

Various additional components often used in pefumery

Such as musk ketone, macrocyclic musk substances such as Musk 174® (12-oxahexadecanolide), Sandela (isocamphylcyclohexanol), polycyclic musk substances such as Fixolid, Galaxolid.

The compounds of formula I can be used in wide limits which can extend in compositions, for example, from 0.1 (detergents)-50% (alcoholic solutions). It will be appreciated that these values are not limiting values, as the experienced perfumer can also achieve effects with even lower concentrations or can synthesize novel complexes with even higher amounts. The preferred concentrations range between 0.5 and 20%. The compositions manufactured with compounds I can be used for all kinds of perfumed consumer goods (eau de cologne, eau de toilette, extracts, lotions, creams, shampoos, soaps, salves, powders, deodorants, detergents, air fresheners, etc).

The compounds I can accordingly be used in the manufacture of compositions and, as will be evident from the above compilation, a wide range of known odorant substances can be used. In the manufacture of such compositions the known odorant substances enumerated above can be used according to methods known to the perfumer, such as e.g. from W. A. Poucher, Perfumes, Cosmetics and Soaps 2, 7th Edition, Chapman and Hall, London, 1974.

EXAMPLE 1

240 g of ethyl 6-hydroxy-hexanoate are placed in a round flask which is provided with a dropping funnel, a thermometer and a stirrer. A mixture of 180 g of acetic anhydride and 3 g of 85% phosphoric acid is added dropwise thereto within a half hour while stirring. During the addition the temperature is held at 25° C. by cooling. Thereafter, the reaction mixture is heated slowly to 50° C. and held at this temperature for 3 hours. After cooling the mixture is treated with ice-water and taken up in 500 ml of hexane. The hexane solution is washed with water, with 100 ml of a 10% sodium carbonate solution and thereupon neutral with water. After drying over sodium sulphate the solvent is distilled off. 282 g of crude product are obtained. Fractional distillation gives 223 g (yield 73.7% of theory) of chemically pure ethyl 6-acetoxy-hexanoate; 190 g thereof can be used as an olfactorily pure product without further treatment.

Further acyloxy-hexanoates $R^2COO(CH_2)_5COOR^1$ (I) are manufactured in an analogous manner starting from the hydroxyesters $HO(CH_2)_5COOR^1$ (II).

The hydroxyesters $HO(CH_2)_5COOR^1$ (II) are accessible from ε-caprolactone and the corresponding $R^1$-alcohol $R^1OH$ in the presence of, e.g., sodium bisulphate ($NaHSO_4$):

|  | B.p. [°C./mmHg] | $n_D^{20}$ |
|---|---|---|
| Methyl 6-hydroxy-hexanoate | 105°/7 | 1.4385 |
| Ethyl 6-hydroxy-hexanoate | 65°/0.001 | 1.4365 |
| Propyl 6-hydroxy-hexanoate | 80°/0.09 | 1.4400 |
| Isopropyl 6-hydroxy-hexanoate | 75°/0.06 | 1.4462 |
| Butyl 6-hydroxy-hexanoate | 85°/0.05 | 1.4412 |
| Isobutyl 6-hydroxy-hexanoate | 92°/0.2 | 1.4396 |
| Allyl 6-hydroxy-hexanoate | 98°/0.25 | 1.4535 |
| Methallyl 6-hydroxy-hexanoate | 99°/0.05 | 1.4580 |

The novel products I and their properties are compiled in the Table A hereinafter.

TABLE A

| Starting material II $R^1$ | Reagent | Product I $R_2$ | $R_1$ | B.p. (mmHg) | $n_D^{20}$ | $d_4^{20}$ | Odour |
|---|---|---|---|---|---|---|---|
| —$CH_2CH_3$ | Acetic anhydride phosphoric acid | $CH_3$— | —$CH_2CH_3$ | 65/0.1 | 1.4292 | 1.0081 | Fruity (raspberries) |

TABLE A-continued

| Starting material II R$^1$ | Reagent | Product I R$_2$ | R$_1$ | B.p. (mmHg) | n$_D^{20}$ | d$_4^{20}$ | Odour |
|---|---|---|---|---|---|---|---|
| —CH$_3$ | Acetic anhydride/ formic acid | H | —CH$_3$ | 107/7 | 1.4310 | 1.0545 | Fruity, after chocolate, iris |
| —CH$_3$ | Acetic anhydride/ phosphoric acid | CH$_3$— | —CH$_3$ | 58/0.08 | 1.4285 | 1.0327 | Fruity (raspberries), flowery |
| —CH$_3$ | Propionic anhydride/ phosphoric acid | CH$_3$CH$_2$— | —CH$_3$ | 122/7 | 1.4318 | 1.0148 | Fruity (raspberries, strawberries), narcissus |
| —CH$_2$CH$_3$ | Acetic anhydride/ formic acid | H | —CH$_2$CH$_3$ | 47/0.04 | 1.4302 | | Fruity (raspberries) |
| —CH$_2$CH$_3$ | Propionic anhydride/ phosphoric acid | CH$_3$CH$_2$— | —CH$_2$CH$_3$ | 114/7 | 1.4304 | 0.9937 | Fruity strawberries, rasberries) |
| —CH$_2$CH$_2$CH$_3$ | Acetic anhydride/ formic acid | H | —CH$_2$CH$_2$CH$_3$ | 52/0.03 | 1.4323 | 1.0104 | Slightly fruity |
| —CH$_2$CH$_2$CH$_3$ | Acetic anhydride/ phosphoric acid | CH$_3$— | —CH$_2$CH$_2$CH$_3$ | 66/0.05 | 1.4310 | 0.9928 | Slightly fruity |
| —CH$_2$CH$_2$CH$_3$ | Propionic anhydride/ phosphoric acid | CH$_3$CH$_2$ | —CH$_2$CH$_2$CH$_3$ | 85.5/0.22 | 1.4335 | | Slightly fruity (raspberries), powdery |
| —CH(CH$_3$)$_2$ | Acetic anhydride/ formic acid | H | —CH(CH$_3$)$_2$ | 68.5/0.2 | 1.4288 | 1.0011 | Fruity (pineapple), flowery |
| —CH(CH$_3$)$_2$ | Acetic anhydride/ phosphoric acid | CH$_3$— | —CH(CH$_3$)$_2$ | 78.5/0.2 | 1.4270 | 0.9847 | Fruity, (raspberries), powdery |
| —CH(CH$_3$)$_2$ | Propionic anhydride/ phosphoric acid | CH$_3$CH$_2$— | —CH(CH$_3$)$_2$ | 67/0.01 | 1.4290 | 0.9733 | Fruity after birch, leather |
| —CH$_2$CH$_2$CH$_2$CH$_3$ | Acetic anhydride/ phosphoric acid | CH$_3$— | —CH$_2$CH$_2$CH$_2$CH$_3$ | 86/0.09 | 1.4330 | 0.9812 | Slightly aldehydic |
| —CH$_2$CH(CH$_3$)$_2$ | Acetic anhydride/ formic acid | H | —CH$_2$CH(CH$_3$)$_2$ | 66/0.11 | 1.4309 | 0.9910 | After hexyl salicylate |
| —CH$_2$CH(CH$_3$)$_2$ | Acetic anhydride/ phosphoric acid | CH$_3$— | —CH$_2$CH(CH$_3$)$_2$ | 74/0.15 | 1.4307 | 0.9765 | Somewhat flowery, after nerolidol |
| —CH$_2$CH=CH$_2$ | Acetic anhydride/ formic acid | H | —CH$_2$CH=CH$_2$ | 69/0.1 | 1.4434 | 1.0344 | Fruity, allylic |
| —CH$_2$CH=CH$_2$ | Acetic anhydride/ phosphoric acid | CH$_3$— | —CH$_2$CH=CH$_2$ | 94/0.09 | 1.4430 | 1.0158 | Fruity |
| —CH$_2$CH=CH$_2$ | Propionic anhydride/ phosphoric acid | CH$_3$CH$_2$— | —CH$_2$CH=CH$_2$ | 87/0.15 | 1.4423 | 1.0014 | Fruity (raspberries), good adhesion |
| —CH$_2$CH$_3$ | Isobutyric anhydride phosphoric acid | (CH$_3$)$_2$CH— | —CH$_2$CH$_3$ | 72/0.1 | 1.4305 | 0.9748 | Fruity (raspberries) |

EXAMPLE 2

160 g of ethyl 6-hydroxy-hexanoate, 145.4 g of N,N-dimethylaniline and 200 ml of anhydrous toluene are placed in a round flask which is provided with a dropping funnel, a thermometer and a stirrer. 119.4 g of ethyl chloroformate are added dropwise at 25° C. within a half hour while stirring. The reaction mixture is held under reflux for 3 hours. After cooling the reaction mixture is poured on to ice-water, the organic phase is washed twice with water, with 100 ml of a 5% hydrochloric acid solution and then neutral with water. After drying over sodium sulphate the solvent is distilled off. 173 g of crude product are obtained. Fractional distillation gives 112 g (yield 48.3% of theory) of chemically pure ethyl 6-ethoxycarbonyloxy-hexanoate; 75 g thereof can be used as an olfactorily pure product without further treatment.

Further alkoxycarbonyloxy-hexanoates R$^2$COO(CH$_2$)$_5$COOR$^1$ (I) with R$^2$=methoxy and ethoxy are manufactured in an analogous manner starting from the hydroxyesters HO(CH$_2$)$_5$COOR$^1$ (II).

The novel products and their properties are compiled in Table B hereinafter.

TABLE B

| Starting material II R$^1$ | Reagent | Product I R$^2$ | R$^1$ | B.p. [°C./mmHg] | n$_D^{20}$ | Odour |
|---|---|---|---|---|---|---|
| —CH$_2$CH$_3$ | ClCOOCH$_2$CH$_3$ | CH$_3$CH$_2$O— | —CH$_2$CH$_3$ | 102°/0.5 | 1.4300 | Fruity, reminiscent of raspberry ketone |
| —CH$_2$CH$_3$ | ClCOOCH$_3$ | CH$_3$O— | —CH$_2$CH$_3$ | 70°/0.02 | 1.4293 | Slightly fruity, after raspberry |
| —CH$_3$ | ClCOOCH$_2$CH$_3$ | CH$_3$CH$_2$O— | —CH$_3$ | 68°/0.05 | 1.4292 | Fruity, after raspberry, oily |
| —CH$_3$ | ClCOOCH$_3$ | CH$_3$O— | —CH$_3$ | 63°/0.02 | 1.4290 | Fruity, after Verdylacetat, slightly reminiscent of green apples, oily |
| —CH$_2$CH$_2$CH$_3$ | ClCOOCH$_2$CH$_3$ | CH$_3$CH$_2$O— | —CH$_2$CH$_2$CH$_3$ | 88°/0.07 | 1.4310 | Slightly reminiscent of raspberry, oily |

TABLE B-continued

| Starting material II | | Product I | | B.p. | | |
|---|---|---|---|---|---|---|
| R$^1$ | Reagent | R$^2$ | R$^1$ | [°C./mmHg] | n$_D^{20}$ | Odour |
| —CH$_2$CH$_2$CH$_3$ | ClCOOCH$_3$ | CH$_3$O— | —CH$_2$CH$_2$CH$_3$ | 78°/0.09 | 1.4308 | Oily, metallic |
| —CH$_2$—CH=CH$_2$ | ClCOOCH$_2$CH$_3$ | CH$_3$CH$_2$O— | —CH$_2$—CH=CH$_2$ | 96°/0.15 | 1.4410 | After raspberry confectionery |

EXAMPLE 3

A. Fruity base in the direction of apple

| | Parts by weight |
|---|---|
| Galaxolid 50 (IFF) (1,3,4,6,7,8-hexahydro-4,6,6,7,8,8-hexamethyl-cyclopenta-γ-2-benzopyran) in diethyl phthalate | 100 |
| Fraise pure (ethyl methyl-phenyl-glycidate) [50% in ethyl phthalate] | 100 |
| Agrumex (Haarmann & Reimer) (2-tert.-butylcyclohexyl acetate) | 60 |
| Maltyl isobutyrate | 30 |
| cis-3-Hexenyl isobutyrate | 60 |
| Dimethylbenzylcarbinyl butyrate | 40 |
| Givescone (Giv) (2-ethyl-6,6-dimethyl-2-cyclohexene-1-carboxylic acid ethyl ester) | 20 |
| Cyclal C (Giv) (1,3-dimethyl-cylohex-1-ene 4(and 5)-carboxaldehyde) (10% DPG) | 10 |
| Ethyl acetoacetate | 40 |
| Dipropylene glycol (DPG) | 440 |
| | 900 |

When 100 parts of ethyl 6-acetoxy-hexanoate are added to the above generally fruity base, the fruity note is brought very clearly in the direction of apple. Moreover, the powdery-fruity note of the Galaxolid-Agrumex complex is underlined in an advantageous manner, which confers to the base a character which is very natural and which has good adhesion.

B. Fruity base in the direction of melon

| | Parts by weight |
|---|---|
| Myraldylacetat (Giv) (5-[3-and 4-(acetoxymethy)-1-cyclohexenyl]-2-methyl-2-pentene) | 100 |
| Linalyl acetate | 100 |
| Dimethylbenzylcarbinyl butyrate | 50 |
| Cyclamen aldehyde | 30 |
| Fraise pure (ethyl methyl-phenyl-glycidate) | 30 |
| Undecalactone | 30 |
| Ethyl acetoacetate | 30 |
| Acetal R (Giv) (acetaldehyde phenyl-ethyl-propyl acetal) | 10 |
| Melonia (3,7-dimethyl-7-methoxy-1-octanal) | 5 |
| Dipropylene glycol (DPG) | 350 |
| | 750 |

By the addition of 100 parts of ethyl 6-acetoxy-hexanoate the above base of general fruity character is brought in the direction of muskmelon. The lactone-like sweet note is clearly intensified, which confers to the base more volume and substantially improved tenacity.

C. Perfumery base in the direction of apricot

| | Parts by weight |
|---|---|
| α-Ionone | 80 |
| Dimethylbenzylcarbinyl butyrate | 50 |
| Allylionone | 40 |
| Fructone$^R$ (IFF) (2-methyl-1,3-dioxolan-2-ethyl acetate) | 30 |
| Palmarosa oil | 20 |
| Undecalactone | 15 |
| Dipropylene glycol (DPG) | 665 |
| | 900 |

An addition of 100 parts of ethyl 6-acetoxy-hexanoate produces in the above conventional apricot base the typical pronounced velvety-soft note of overripe apricots; the resulting formulation is already well suited for the perfuming of cosmetic preparations; in other words; the base which results is now a true, complete perfume base. In the case of the conventional apricot base this is not the case as, although it can also produce an apricot nuance in a composition, the sweet, velvety note of the ripe fruit is subsequently missing in the composition.

D. Flowery-green base

| | Parts by weight |
|---|---|
| Phenoxyethyl alcohol | 205 |
| Linalool | 150 |
| Terpineol | 100 |
| Dimethylbenzylcarbinyl butyrate | 60 |
| Calaxolid (IFF) (1,3,4,6,7,8-hexahydro-4,6,6,7,8,8-hexamethyl-cyclopenta-γ-2-benzopyran) | |
| Hedione (Firmenich) (methyl dihydrojasmonate) | 60 |
| Verdylacetat (dihydro-nor-dicyclo-pentadienyl acetate) | 50 |
| Citronellol | 40 |
| Acetal R (Giv) (acetaldehyde phenyl-ethyl n-propyl acetal) | 30 |
| Geranyl acetate | 30 |
| Lilial (Giv) (p-tert.butyl-α-methylhydrocinnamaldehyde) | 15 |
| Cyclamen aldehyde (10% DPG) | 10 |
| Cyclal C (Giv) (1,3-dimethyl-cyclohex-1-ene 4(and 5)-carboxaldehyde) (10% DPG) | 10 |
| Phenylacetaldehyde dimethyl acetal | 10 |
| Corps cassis (Giv) (p-menthane-8-thiol-3-one (10% DPG) | 10 |
| Eugenol | 10 |
| Diphenyl oxide | 5 |
| Indole (10% DPG) | 5 |
| Dipropylene glycol (DPG) | 40 |
| | 900 |

When 100 parts of ethyl 6-acetoxy-hexanoate are added to the above flowery-green base, there results a base which is very much greener, more powdery and substantially stronger in odour. The novel ester combines the musk and the green notes (Galaxolid-Acetal R) with one another very advantageously. The base is very well suited for the perfuming of cosmetic preparations.

E. Herby-green base

|  | Parts by weight |
|---|---|
| Linalyl acetate | 150 |
| Madrox (Giv) (1-methyl-1-methoxy-cyclododecane) | 100 |
| Linalool | 150 |
| Tetrahydrolinalool | 80 |
| Hedione (Firmenich) (methyl dihydrojasmonate) | 100 |
| Bergamot oil | 80 |
| Hyssop oil | 60 |
| Patchouli oil (anhydrous) | 60 |
| Galaxolid (IFF) (1,3,4,6,7,8-hexahydro-4,6,6,7,8,8-hexamethyl-cyclopenta-α-2-benzopyran) | 40 |
| Allylionone | 20 |
| Eugenyl phenylacetate | 20 |
| Acetal E (Giv) (1-phenyl-4-methyl-3,5-dioxyheptane) | 15 |
| Cyclal C (Giv) (1,3-dimethyl-cyclohex-1-ene 4(and 5)-carboxaldehyde) (10% DPG) | 10 |
| Corps cassis (Giv) (p-methane-8-thio-3-one) (10% DPG) | 10 |
| Fixateur 404 (Firmenich) (8-α, 12-oxido-13,14,15,16-tetranorlabdane) | 5 |
|  | 900 |

By the addition of 10% of ethyl 6-acetoxy-hexanoate the herby-green note of the above base is clearly intensified. Ethyl 6-acetoxy-hexanoate underlines the somewhat powdery, spicy note of the basic composition in an unsuspected manner, which brings more warmth and volume to the base. The novel formulation can now be used very well for men's colognes.

On the other hand, in not one of the above bases A to E can the effects specified be realized by replacing ethyl 6-acetoxy-hexanoate by the same amounts of the structurally similar compounds diethyl adipate or 1,6-diacetoxyhexane.

EXAMPLE 4

A. Herby-green base

|  | Parts by weight |
|---|---|
| Fixateur 404 | 5 |
| Corps Cassis DC (10% DPG) | 10 |
| Cyclal C (10% DPG) | 10 |
| Acetal E | 15 |
| Eugenyl phenylacetate | 20 |
| Ketone V (allyl-α-ionone) | 20 |
| Galaxolid 50 | 40 |
| Patchouli anhydrous | 60 |
| Hyssop oil | 60 |
| Bergamot oil | 80 |
| Tetrahydrolinalool | 80 |
| Madrox | 100 |
| Hedione | 100 |
| Linalool | 150 |
| Linalyl acetate | 150 |
|  | 900 |

The addition of 100 parts of ethyl 6-ethoxycarbonyloxy-hexanoate intensifies the fruity-hesperidin aspect of the base and confers remarkable freshness to the novel composition. Compared with the composition without the addition, the novel composition is quite clearly preferred.

B. Fruity base

|  | Parts by weight |
|---|---|
| Cyclal C (10% DPG) | 10 |
| Givescone | 20 |
| Maltyl isobutyrate | 30 |
| Dimethylbenzylcarbinyl butyrate | 40 |
| Ethyl acetate | 40 |
| cis-3-Hexenyl isobutyrate | 60 |
| Agrumex | 60 |
| Galaxolid 50 | 100 |
| Fraise pure | 100 |
| Dipropylene glycol (DPG) | 440 |
|  | 900 |

An addition of 100 parts of ethyl 6-ethoxycarbonyloxy-hexanoate leads to an unequivocal preference for the thus-prepared novel composition, as in it the desired effect in the direction of apple can be recognized substantially clearer than in the original base without the addition. A desired stylizing of a primary general-fruity note is therefore brought about by the addition of the novel compound I, the strawberry aspect ("fraise pure") changing into an apple note. Furthermore, this effect is unexpected, as the novel compound I has a fruity smell in the direction of raspberry, and therefore rather an intensification of the fruity-berry like note would have been expected.

Base in the direction of melon

|  | Parts by weight |
|---|---|
| Melonia | 5 |
| Acetal R | 10 |
| Ethyl acetate | 30 |
| Geranyl acetate | 30 |
| Peche Pure (γ-n-heptylbutyrolactone) | 30 |
| Fraise Pure | 30 |
| Cyclamen aldehyde | 30 |
| Dimethylbenzylcarbinyl butyrate | 50 |
| Myraldylacetate | 100 |
| Linalyl acetate | 100 |
| Dipropylene glycol (DPG) | 350 |
|  | 765 |

The addition of 100 parts of ethyl 6-ethoxycarbonyloxy-hexanoate to the above base is extraordinarily favourable from the organoleptic point of view, as the fruity-juicy melon character is thereby significantly accentuated.

We claim:

1. A compound of the formula

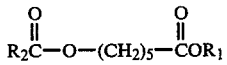

wherein:
R₁ is chosen from the group consisting of alkyl radicals having one to four carbon atoms and alkenyl radicals having two to four carbon atoms, and
R₂ is chosen from the group consisting of hydrogen, alkyl radicals having one to three carbon atoms, methoxy and ethoxy.

2. A compound according to claim 1 wherein R₁ is methyl, ethyl, propyl, butyl or allyl, and R₂ is hydrogen, methyl, ethyl, propyl, butyl, or ethoxy.

3. A compound according to claim 2 wherein R₁ is ethyl or allyl.

4. A compound according to claim 3 wherein $R_1$ is ethyl and $R_2$ is methyl.

5. A compound according to claim 3 wherein $R_1$ is ethyl and $R_2$ is isopropyl.

6. A compound according to claim 3 wherein $R_1$ is allyl and $R_2$ is ethyl.

7. A compound according to claim 3 wherein $R_1$ is ethyl and $R_2$ is ethoxy.

8. A fragrance composition which comprises an olfactory effective amount of a compound of the formula

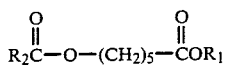

wherein:
$R_1$ is chosen from the group consisting of alkyl radicals having one to four carbon atoms and alkenyl radicals having two to four carbon atoms, and
$R_2$ is chosen from the group consisting of hydrogen, alkyl radicals having one to three carbon atoms, methoxy and ethoxy
and at least one other fragrance ingredient.

9. A composition according to claim 8 wherein
$R_1$ is methyl, ethyl, propyl, butyl or allyl, and
$R_2$ is hydrogen, methyl, ethyl, propyl, butyl or ethoxy.

10. A composition according to claim 9 wherein $R_1$ is ethyl and $R_2$ is methyl.

11. A composition according to claim 9 wherein $R_1$ is ethyl and $R_2$ is isopropyl.

12. A composition according to claim 9 wherein $R_1$ is allyl and $R_2$ is ethyl.

13. A composition according to claim 9 wherein $R_1$ is ethyl and $R_2$ is ethoxy.

14. A method for improving the odor of fragrance compositions wherein the improvement comprises adding thereto an olfactory effective amount of a compound of the formula

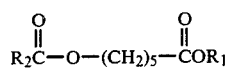

wherein:
$R_1$ is chosen from the group consisting of alkyl radicals having one to four carbon atoms and alkenyl radicals having two to four carbon atoms, and
$R_2$ is chosen from the group consisting of hydrogen, alkyl radicals having one to three carbon atoms, methoxy and ethoxy.

15. A method according to claim 14 wherein
$R_1$ is methyl, ethyl, propyl, butyl or allyl, and
$R_2$ is hydrogen, methyl, ethyl, propyl, butyl or ethoxy.

16. A method according to claim 15 wherein $R_1$ is ethyl and $R_2$ is methyl.

17. A method according to claim 15 wherein $R_1$ is ethyl and $R_2$ is isopropyl.

18. A method according to claim 15 wherein $R_1$ is allyl and $R_2$ is ethyl.

19. A method according to claim 15 wherein $R_1$ is ethyl and $R_2$ is ethoxy.

* * * * *